US00PP14192P29

(12) United States Plant Patent
Westhoff

(10) Patent No.: US PP14,192 P2
(45) Date of Patent: Sep. 30, 2003

(54) VARIETY OF SUTERA PLANT NAMED 'WESBABLUE'

(50) Latin Name: *Sutera cordata*
Varietal Denomination: 'Wesbablue'

(75) Inventor: Heinrich Westhoff, Fresenhorst 22-24, 46354 Südlohn/Oeding (DE)

(73) Assignees: Heinrich Westhoff (DE); Josef Westhoff (DE)

( * ) Notice: Subject to any disclaimer, the term of this patent is extended or adjusted under 35 U.S.C. 154(b) by 0 days.

(21) Appl. No.: 10/341,703
(22) Filed: Jan. 14, 2003
(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Webb Ziesenheim Logsdon Orkin & Hanson, P.C.

(57) ABSTRACT

A new and distinct early flowering Sutera plant with intense violet-blue colored flowers and vigorous growth.

2 Drawing Sheets

Botanical classification: *Sutera cordata.*
Varietal denomination: 'Wesbablue'.

BACKGROUND OF THE INVENTION

The present invention comprises a new and distinct cultivar of Sutera plant known by the varietal name 'Wesbablue'. The new variety was discovered in 2001 in a selected breeding program in Südlohn, Germany designed to produce a new compact and rich blooming blue Sutera variety. The new variety was selected from a cross of proprietary unpatented breeding plants Bacopa 00FA56 (female parent) and Bacopa 00FA021 (male parent). The new variety has shorter internodes, larger flowers, and a more spherical plant shape than the female parent but with similar leaves and flower color. Compared to the male parent, the new variety has shorter internodes, smaller flowers, larger leaves, and more branching but with similar flower color.

The new variety was first asexually reproduced in 2001 by cuttings in Südlohn, Germany. The new variety has been trial and field tested at Südlohn and has been found to retain its distinctive characteristics and remain true to type through successive propagations.

The following traits in combination distinguish 'Wesbablue' as a new and distinct cultivar:

1. Rich blooming plant, covered in flowers.
2. Attractive light violet-blue flowers.
3. Symmetrical growth, short internodes.
4. Cascading but rounded plant habit.
5. Plants have a good appearance from a distance.
6. Dark green leaves.
7. Short peduncles.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
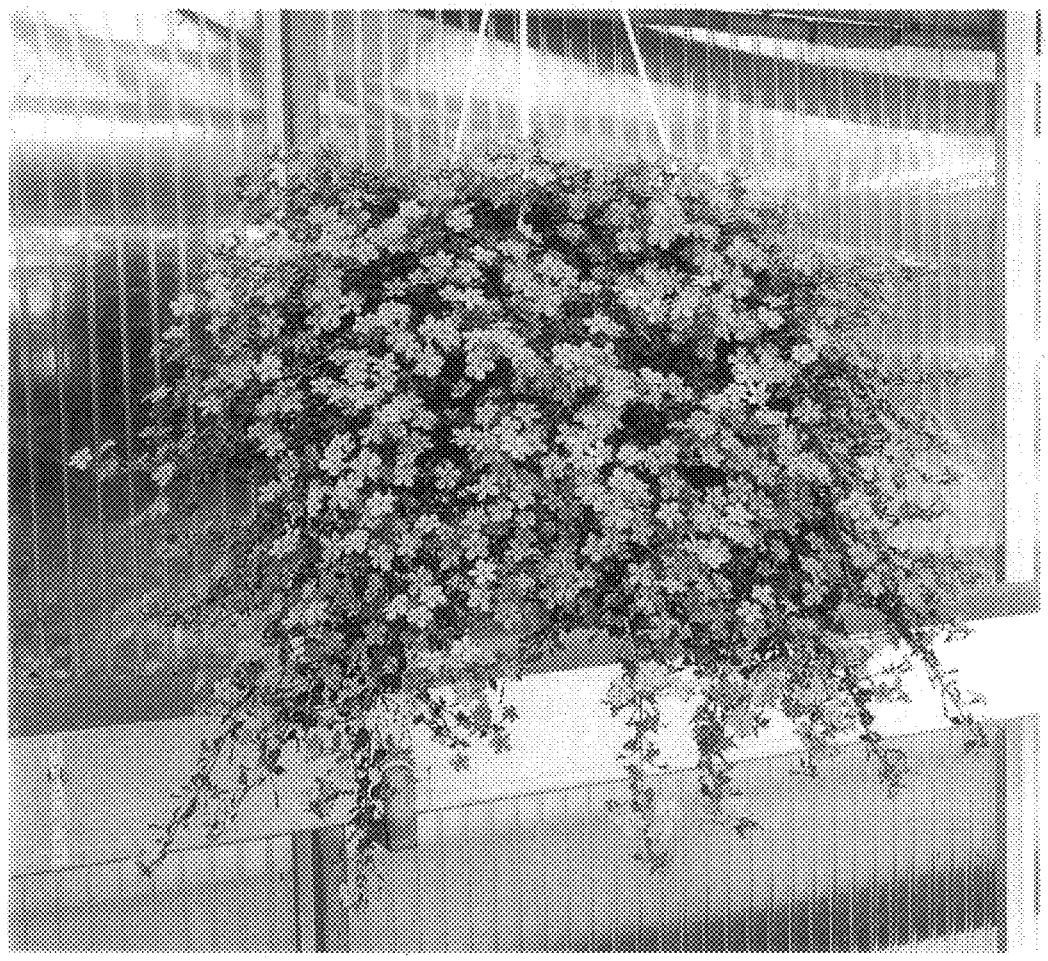
FIG. 1 is a photograph of the plant.
Figure 2:
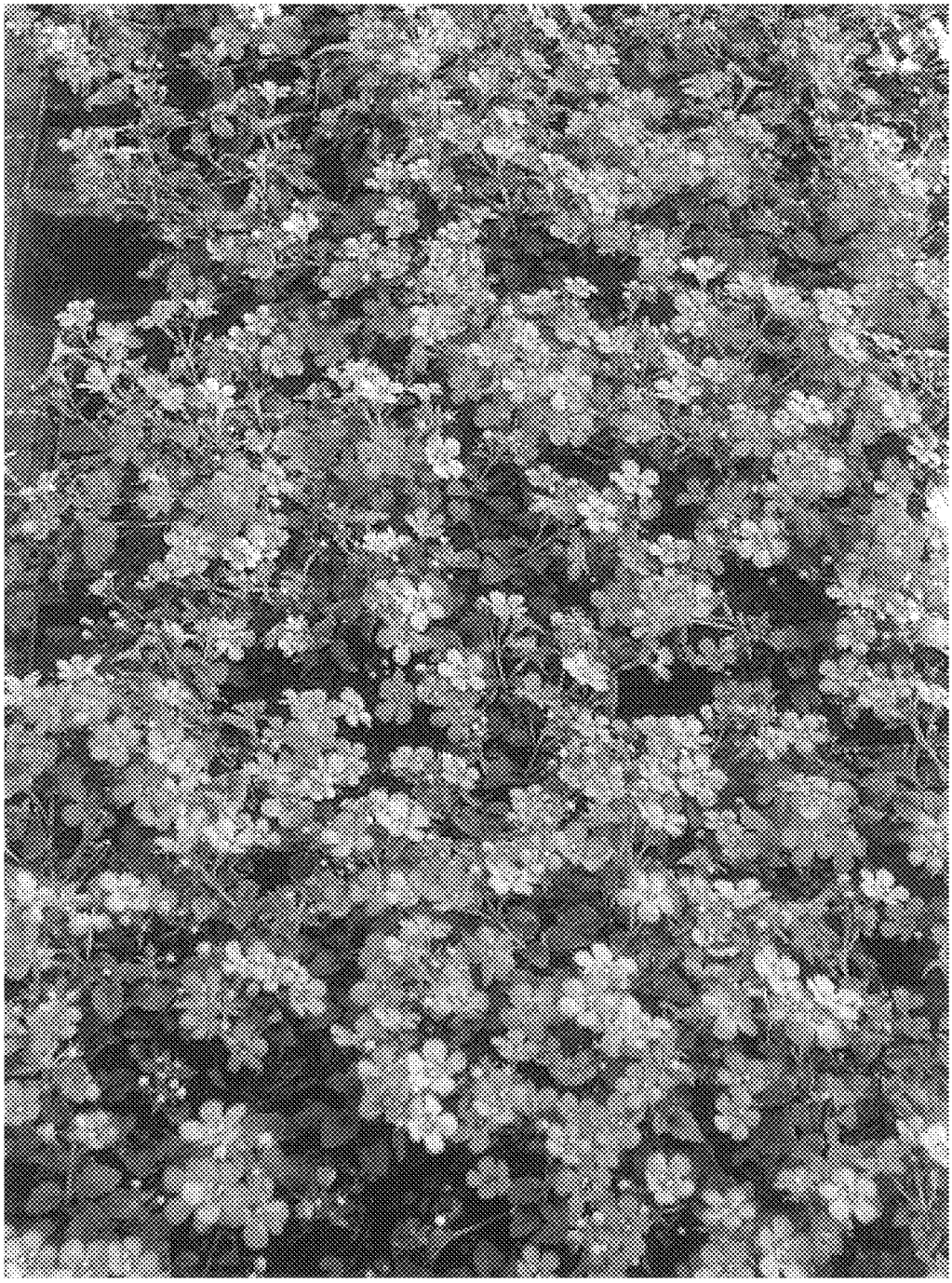
FIG. 2 is a close up view of the blooms of the new plant.

The following detailed description sets forth characteristics of the new cultivar. The data which defines these characteristics were collected by asexual reproductions by cuttings carried out in Südlohn, Germany. Flowering plants were produced in 12–15 weeks without growth retardants and were grown in 12 cm containers with pinching 3–4 weeks after potting. Plants for the description were 20 weeks old, grown in a greenhouse at 20–25° C. daytime temperature and at 16–18° C. night temperature with light levels of 3,000–50,000 lux. The color readings were taken on a plant outdoors and in a greenhouse under natural light. Color references are primarily to The 2001 R.H.S. Colour Chart of The Royal Horticultural Society of London.

Compared to 'Wesbavio'(Copending U.S. Plant patent application No. 10/037,717) the new variety has shorter internodes, shorter branches, larger leaves, shorter flower tubes, larger sepals, and short peduncles. Compared to the unpatented variety 'Seamist', the new variety is shorter and more compact with shorter internodes, larger flowers, larger sepals, and a more intense flower color.

PLANT

Form: Hanging with a compact, spherical shape.
Size: 11 cm from soil to top of flowers; 40 cm wide.
Roots:
- *Habit.*—Fine; fibrous; well-branched.
- *Time to initiate roots.*—About 14–16 days at 20° C.
- *Time to produce a rooted cutting or liner.*—About 24–28 days at 20° C.

Main stem: 40 cm long; 2.2 mm diameter; colored 146B with some reddish anthocyanin; very short dense pubescence.
Branching habit: Generally 1 branch per node with pinching.
Lateral branches:
- *Texture.*—Pubescent (very short, dense hairs).
- *Diameter.*—1.1 mm.
- *Length.*—16–20 cm.
- *Internode length.*—1.4 cm.
- *Quantity.*—1–2 per node.
- *Color.*—146B.

Foliage:
*Arrangement.*—Opposite.
*Size of leaf.*—Length: 1.6–1.7 cm. Width: 1.1–1.2 cm.
*Shape of leaf.*—Ovate to round.
*Shape of apex.*—Acute.
*Shape of base.*—Attenuate.
*Texture.*—Smooth.
*Pubescence.*—Very little; very fine.
*Aspect.*—Flat.
*Margin.*—Dentate.
*Color.*—Young leaves: Upper surface: 146A. Lower surface: 146B. Mature leaves: Upper surface: 147A. Lower surface: 147B.
*Petioles.*—Length: 3.1 mm. Diameter: 1 mm. Color: 147B.
*Venation.*—Pinnate; color same as mature leaves.

FLOWER

Natural flowering season: Spring through autumn; tolerates temperature between 4° to 30° C.
Flower type and habit: Single, salverform, persistent; abundant.
Fragrance: None.
Flower size:
*Length.*—0.71 cm.
*Width.*—1.45 cm.
*Tube length.*—0.65 cm.
*Tube diameter.*—0.1 cm at base; 0.35 cm at top.
Corolla:
*Aspect.*—Almost flat.
*Petal length from throat.*—6 mm.
*Petal width.*—5.3 mm.
*Petal quantity.*—5, fused.
*Petal shape.*—Broad; slightly angular.
*Petal apex.*—Obtuse.
*Petal margin.*—Entire.
*Appearance.*—Dull.
*Color.*—Petals: When opening: Upper surface: 90C. Lower surface: N82D and 84D. Fully opened: Upper surface: Varying between 90C and 90D and N87A and N87C, changing to 90C over time. Lower surface: N87C and 85C. Flower throat inside surface: 25A with ring between 150C and 150D. Flower eye: 25A. Flower tube: Outside: Top: 92D. Middle: 23A. Base: 150C. Veins: Not veined.

Calyx:
*Arrangement.*—Whorled.
Sepals:
*Shape.*—Linear.
*Width.*—1 mm.
*Length.*—5.3 mm.
*Margin.*—Entire.
*Apex.*—Acute.
*Texture.*—Pubescent.
*Appearance.*—Dull.
*Color.*—Upper surface: 146B, varying with 137C to 137B. Lower surface: 137B.
Bud:
*Shape.*—Oblanceolate.
*Length.*—6.9 cm.
*Diameter.*—3.5 mm.
*Color.*—Tip: 85B. Middle: Between 12B and 12C. Base: 150C.
Peduncle:
*Length.*—0.6 cm.
*Diameter.*—0.75 mm.
*Color.*—146B.
*Orientation.*—Acute angle.
*Strength.*—Flexible.

REPRODUCTIVE ORGANS

Stamens:
*Quantity.*—4; on two plains (2 high, 2 low); fused with petals.
*Anthers.*—Shape: Flat, reniform. Length: 0.8 mm. Width: 1.5 mm. Color: 21A.
*Pollen.*—Color: 21A. Amount: Moderate.
Pistil:
*Quantity.*—1.
*Length.*—0.85 cm.
*Style.*—Length: 5.5 mm. Color: 150C.
*Stigma.*—Shape: Long; curved inwardly. Color: 144A. Ovary color: 144B.
Seeds: Generally none.
Disease/pest resistance: No susceptibility to diseases or pests has been noted to date.
Garden performance: Plant tolerates rain and wind.

I claim:

1. A new and distinct variety of Sutera plant substantially as shown and described.

* * * * *